United States Patent
Hyun et al.

(10) Patent No.: US 10,561,403 B2
(45) Date of Patent: Feb. 18, 2020

(54) SENSOR COORDINATE CALIBRATION IN AN ULTRASOUND SYSTEM

(71) Applicant: SAMSUNG MEDISON CO., LTD., Hongcheon-gun (KR)

(72) Inventors: Dong Gyu Hyun, Gwangju-si (KR); Jong Beom Ra, Daejeon (KR); Dughoon Lee, Daejeon (KR); Woo Hyun Nam, Busan (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 16/362,011

(22) Filed: Mar. 22, 2019

(65) Prior Publication Data

US 2019/0216435 A1 Jul. 18, 2019

Related U.S. Application Data

(63) Continuation of application No. 15/943,061, filed on Apr. 2, 2018, now Pat. No. 10,271,822, which is a (Continued)

(30) Foreign Application Priority Data

Jul. 31, 2009 (KR) .................. 10-2009-0070994

(51) Int. Cl.
*G06K 9/00* (2006.01)
*A61B 8/08* (2006.01)
(Continued)

(52) U.S. Cl.
CPC ............ *A61B 8/5207* (2013.01); *A61B 6/032* (2013.01); *A61B 6/5247* (2013.01);
(Continued)

(58) Field of Classification Search
USPC ................................... 382/128–134
See application file for complete search history.

(56) References Cited

U.S. PATENT DOCUMENTS 5,640,956 A 6/1997 Getzinger et al.
6,775,404 B1 8/2004 Pagoulatos et al.
(Continued)

FOREIGN PATENT DOCUMENTS

EP 1196089 A2 4/2002
EP 1467317 A1 10/2004
(Continued)

OTHER PUBLICATIONS

Nam et al.: "Anatomical feature extraction in 3D B-mode ultrasound liver images for CT-ultrasound image registration", Int. J CARS, vol. 3 (Suppl. 1), pp. S401-S402, 2008, http://www.isl.kaist.ac.kr/papers/IC/ic120.pdf.
(Continued)

*Primary Examiner* — Alex Kok S Liew
(74) *Attorney, Agent, or Firm* — Sughrue Mion, PLLC

(57) ABSTRACT

A medical imaging apparatus includes: an ultrasound probe to transmit and receive an ultrasound signal to obtain an ultrasound image of an object; a sensor coupled to the ultrasound probe to provide a position information related to an ultrasound imaging position in the object; and a processor to extract a certain anatomical feature from the ultrasound image and the certain anatomical feature from a medical image, perform a first registration between the medical image and the ultrasound image by matching the certain anatomical feature in the ultrasound image the certain anatomical feature in the medical image, perform a second registration between the sensor and the medical image based on the position information and the first registration, and control a display to display a portion of the medical image corresponding to the ultrasound imaging position based on
(Continued)

at least one of the first registration and the second registration.

20 Claims, 5 Drawing Sheets

Related U.S. Application Data continuation of application No. 14/752,165, filed on Jun. 26, 2015, now Pat. No. 9,955,951, and a continuation of application No. 12/846,545, filed on Jul. 29, 2010, now Pat. No. 9,082,178.

(51) Int. Cl.
| | |
|---|---|
| A61B 6/00 | (2006.01) |
| A61B 8/00 | (2006.01) |
| G06T 7/33 | (2017.01) |
| G06T 7/11 | (2017.01) |
| G01S 15/89 | (2006.01) |
| A61B 6/03 | (2006.01) |
| G06T 11/00 | (2006.01) |

(52) U.S. Cl.
CPC .......... *A61B 8/0833* (2013.01); *A61B 8/0891* (2013.01); *A61B 8/4254* (2013.01); *A61B 8/4416* (2013.01); *A61B 8/4444* (2013.01); *A61B 8/461* (2013.01); *A61B 8/469* (2013.01); *A61B 8/483* (2013.01); *A61B 8/488* (2013.01); *A61B 8/5223* (2013.01); *A61B 8/5261* (2013.01); *A61B 8/58* (2013.01); *G01S 15/899* (2013.01); *G06T 7/11* (2017.01); *G06T 7/33* (2017.01); *G06T 7/337* (2017.01); *G06T 11/00* (2013.01); *A61B 6/03* (2013.01); *G06T 2207/10028* (2013.01); *G06T 2207/10081* (2013.01); *G06T 2207/10136* (2013.01); *G06T 2207/20221* (2013.01); *G06T 2207/30056* (2013.01); *G06T 2207/30101* (2013.01)

(56) References Cited

U.S. PATENT DOCUMENTS

| | | | |
|---|---|---|---|
| 8,734,349 | B2 | 5/2014 | Kruecker et al. |
| 9,082,178 | B2 | 7/2015 | Hyun et al. |
| 9,955,951 | B2 | 5/2018 | Hyun |
| 2005/0089205 | A1 | 4/2005 | Kapur et al. |
| 2007/0242069 | A1* | 10/2007 | Matsue ................ G06F 19/321 345/428 |
| 2008/0009724 | A1 | 1/2008 | Lee et al. |
| 2008/0095421 | A1 | 4/2008 | Sun |
| 2008/0247622 | A1 | 10/2008 | Aylward et al. |
| 2009/0067752 | A1 | 3/2009 | Lee et al. |
| 2009/0285460 | A1 | 11/2009 | Ishikawa et al. |
| 2010/0268085 | A1 | 10/2010 | Kruecker et al. |
| 2014/0270424 | A1 | 9/2014 | Piper |

FOREIGN PATENT DOCUMENTS

| | | | |
|---|---|---|---|
| JP | 2003-527880 | A | 9/2003 |
| JP | 2005-125080 | A | 5/2005 |
| JP | 2006217939 | A | 8/2006 |
| JP | 2007-244575 | A | 9/2007 |
| JP | 2009-071821 | A | 4/2009 |
| JP | 2009-273597 | A | 11/2009 |
| JP | 2011502681 | A | 1/2011 |
| JP | 2011502687 | A | 1/2011 |
| KR | 10-2007-0110965 | A | 11/2007 |
| KR | 10-2008-0053057 | A | 6/2008 |
| WO | 2006-092602 | A1 | 9/2006 |
| WO | 2009-063361 | A1 | 5/2009 |
| WO | 2009-063423 | A1 | 5/2009 |

OTHER PUBLICATIONS

Pitot et al.: "Piecewise Affine Registration of Biological Images for Volume Reconstruction", Medical Image Analysis, Elsevier, 19 pages.
Japanese Notice of Allowance issued in corresponding Japanese Application No. 2010-168405, dated Aug. 5, 2014, with English translation.
Korean Office Action issued in Korean Application No. 10-2009-00700994, dated Sep. 20, 2011.
Huang et al.: "Dynamic 2D Ultrasound and 3D CT Image Registration of the Beating Heart", IEEE Transactions on Medical Imaging, vol. 28, No. 8, pp. 1179-1189, 2009, http://ieeexplore.ieee.org/stamp/atamp.jsp?arnumber=04738379.
Extended European Search Report for EP 10169834.8-2319, dated Oct. 26, 2010, 6 pages.
Japanese Office Action issued in Japanese Application No. 2010-168405 dated Mar. 18, 2014.
Korean Notice of Allowance issued in Korean Application No. 10-2009-00700994, dated Feb. 3, 2012.
Bortfeld et al.: "Effects of intra-fraction motion on IMRT dose delivery: statistical analysis and simulation", Phys. Med. Biol. 47, pp. 2203-2220, (2002).

* cited by examiner

SENSOR COORDINATE CALIBRATION IN AN ULTRASOUND SYSTEM

CROSS-REFERENCE TO RELATED APPLICATIONS

The present application is a Continuation of U.S. patent application Ser. No. 15/943,061, filed Apr. 2, 2018, which is a Continuation of U.S. application Ser. No. 14/752,165, filed Jun. 26, 2015, now U.S. Pat. No. 9,955,951 issued May 1, 2018, which is a Continuation of U.S. application Ser. No. 12/846,545, filed Jul. 29, 2010, now U.S. Pat. No. 9,082,178 issued Jul. 14, 2015, which claims priority from Korean Patent Application No. 10-2009-0070994, filed Jul. 31, 2009. The disclosure of each of these applications is incorporated herein by reference in its entirety.

TECHNICAL FIELD

The present invention generally relates to ultrasound systems, and more particularly to an ultrasound system and method for performing sensor coordinate calibration through image-based registration between a three-dimensional ultrasound image and a computed tomography (CT) image.

BACKGROUND

The ultrasound system has become an important and popular diagnostic tool due to its non-invasive and non-destructive nature. Modern high-performance ultrasound imaging diagnostic systems and techniques are commonly used to produce two- or three-dimensional images of internal features of patients (target objects).

However, the ultrasound system suffers from inherent shortcomings of an ultrasound image such as a low signal-to-noise ratio and a limited field of view. Thus, the image registration of a CT (or MR) image onto the ultrasound image has been introduced in order to compensate for deficiencies of the ultrasound image. A sensor has been used to perform the image registration of a CT (or MR) image onto the ultrasound image. Researches have been introduced to calibrate the sensor to match coordinates of the CT image and coordinates of the sensor.

Conventionally, after outer markers are attached on a surface of a target object, a CT image and an ultrasound image for the target object with the markers are acquired. Thereafter, the calibration is carried out by using a relationship between coordinates of the markers in the CT and ultrasound image. That is, the outer markers should be attached to the surface of the target objects before obtaining the CT image and the ultrasound image and be maintained in the same position until completing the acquisition of the ultrasound image. Moreover, a sensor must sense the positions of the respective outer markers.

Further, the registration between the coordinate of the CT image and the coordinate of the sensor has been performed by manually inputting inner markers on the CT image. Thus, a user of the ultrasound system had to input the inner markers, which causes the registration between the coordinate of the CT image and the coordinate of the sensor to be wrong.

SUMMARY

An embodiment for forming a plurality of three-dimensional ultrasound images is disclosed herein. In one embodiment, by way of non-limiting example, an ultrasound system, includes: an ultrasound image forming unit including a ultrasound probe and being configured to form a three-dimensional ultrasound image of a target object; a sensor coupled to the ultrasound probe; a memory configured to store a three-dimensional computed tomography (CT) image of the target object and position information on a position between the three-dimensional ultrasound image and the sensor; and a processor configured to perform image registration between the three-dimensional CT image and the three-dimensional ultrasound image to thereby form a first transformation function for transforming a position of the sensor to a corresponding position on the three-dimensional CT image and perform calibration of the sensor by applying the position information to the first transformation function.

In another embodiment, a method of performing a calibration of a sensor, includes: a) obtaining a three-dimensional ultrasound image of a target object obtained by the ultrasound system and a three-dimensional CT image; b) calculating a position information on a position between the three-dimensional ultrasound image and the sensor; c) performing registration between the three-dimensional ultrasound image and the three-dimensional CT image to obtain a first transformation function for transforming a position of the sensor to a corresponding position on the three-dimensional CT image; and d) performing calibration of the sensor by applying the position information to the first transformation function.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
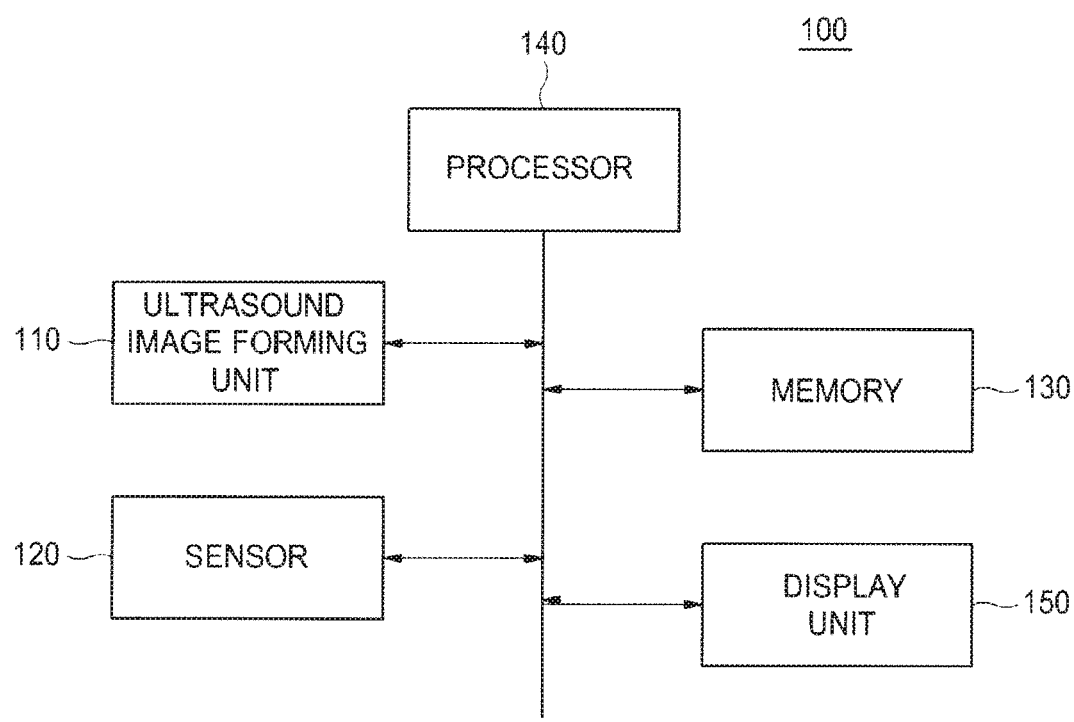
FIG. 1 is a block diagram showing an illustrative embodiment of an ultrasound system.

FIG. 1 is a block diagram showing an illustrative embodiment of an ultrasound system. The ultrasound system 100 may include an ultrasound image forming unit 110, a sensor 120, a memory 130, a processor 140 and a display unit 150.

The ultrasound image forming unit 110 may be configured to transmit ultrasound signals to a target object (not shown) and receive ultrasound echo signals reflected from the target object. The ultrasound image forming unit 110 may be further configured to form a three-dimensional ultrasound image of the target object based on the received ultrasound echo signals.

Figure 2:
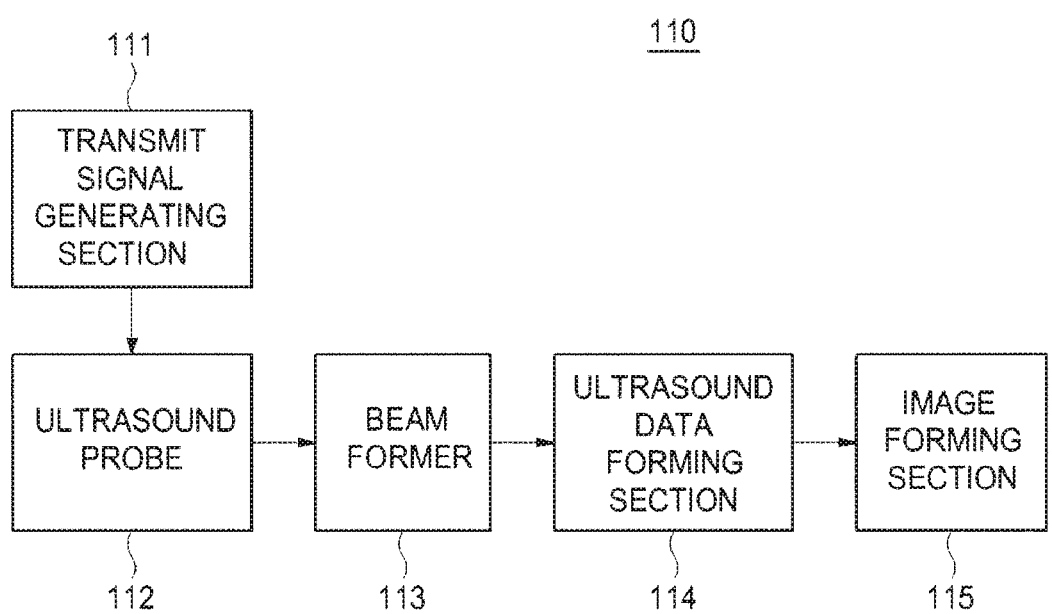
FIG. 2 is a block diagram showing an illustrative embodiment of an ultrasound image forming unit.

FIG. 2 is a block diagram showing an illustrative embodiment of an ultrasound image forming unit 110. The ultrasound image forming unit 110 may include a transmit (Tx) signal generating section 111, an ultrasound probe 112 including a plurality of transducer elements (not shown), a beam former 113, an ultrasound data forming section 114 and an image forming section 115.

The Tx signal generating section 111 may generate Tx signals according to an image mode set in the ultrasound system 100. The image mode may include a brightness (B) mode, a Doppler (D) mode, a color flow mode, etc. In one exemplary embodiment, the B mode may be set in the ultrasound system 100 to obtain a B mode ultrasound image.

The ultrasound probe 112 may receive the Tx signals from the Tx signal generating section 111 and generate ultrasound signals, which may travel into the target object. The ultrasound probe 112 may further receive ultrasound echo signals reflected from the target object and convert them into electrical receive signals. In such a case, the electrical receive signals may be analog signals. The ultrasound probe 112 may be a three-dimensional probe, a two-dimensional probe, a one-dimensional probe or the like.

Figure 3:
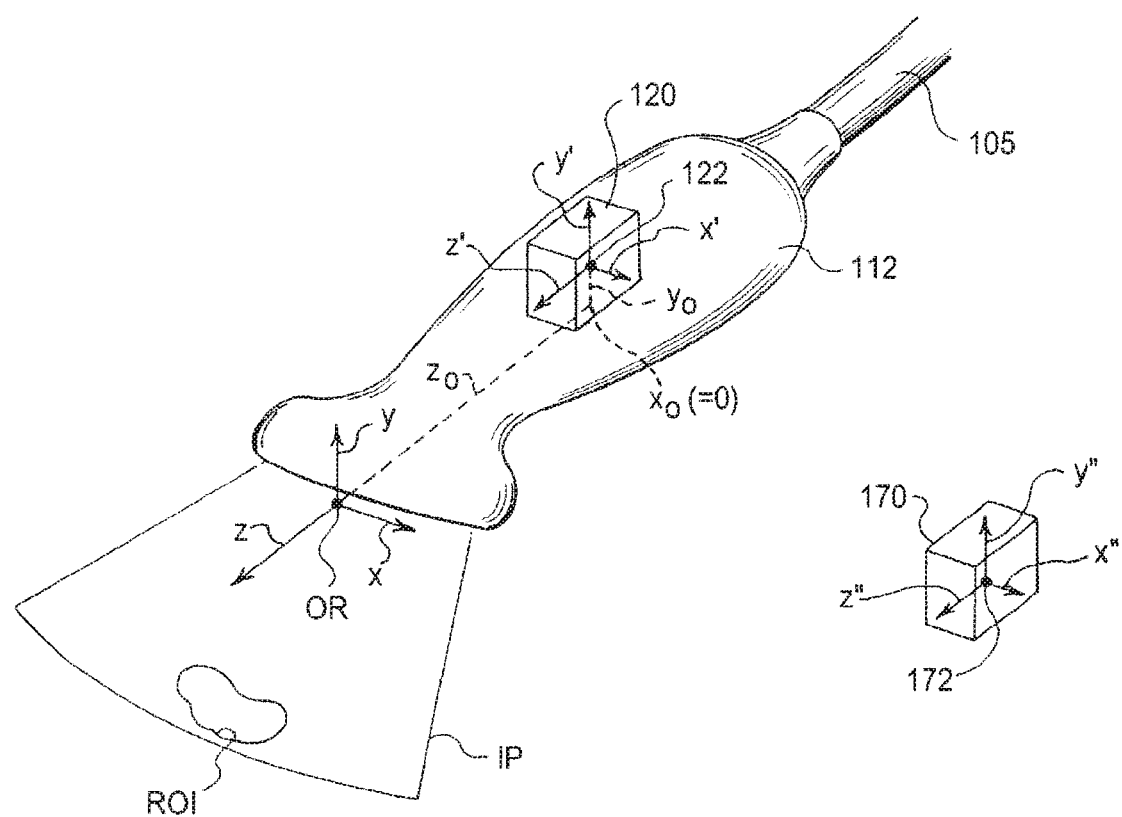
FIG. 3 is an illustrative embodiment of an ultrasound probe.

FIG. 3 is an illustrative embodiment of an ultrasound probe 112. At least one transducer element (not shown) of the ultrasound probe 112 generates an image plane IP, which is used to scan a region of interest ROI. The image plane IP may be one of slice planes of the three-dimensional ultrasound image. The sensor 120 is attached to the housing of the ultrasound probe 112 to determine the position and orientation of the image plane IP. The ultrasound system 100 coupled with the ultrasound probe 112 via the probe cable 105 can use the data generated by the sensor 120 to determine the position and orientation of the sensor 120 and/or the image plane IP, as described below.

In this preferred embodiment, the sensor 120 is a magnetic sensor that monitors the free-hand movement of the ultrasound probe 112 in six degrees of freedom with respect to a transducer element 170. As shown in FIG. 3, the sensor 120 and the transducer element 170 each define an origin (122, 172, respectively) defined by three orthogonal axes (X', Y', Z' and X", Y", Z", respectively). The sensor 120 monitors the translation of the origin 122 with respect to the origin 172 of the transducer element 170 to determine position and monitor the rotation of the X', Y', Z' axes with respect to the X", Y", Z" axes of the transducer element 170 to determine orientation.

The position and orientation of the sensor 120 can be used to determine the position and orientation of the image plane IP. As shown in FIG. 3, the image plane IP defines an origin OR defined by three orthogonal axes X, Y, Z, which are preferably aligned with the origin of a center acoustic line generated by the ultrasound probe 112. The position of the origin 122 and the orientation of axes X', Y', Z' of the sensor 120 may not precisely coincide with the position of the origin OR and the orientation of the axes X, Y, Z of the image plane IP. For example, in FIG. 3, the origin OR of the image plane IP is offset from the origin 122 of the sensor 120 by a distance $z_0$ along the Z-direction and a distance of $y_0$ along the Y-direction. In FIG. 3, there is no offset along the X-direction nor is there a rotational offset in the orientation of the axes. Accordingly, the position and orientation of the sensor 120 do not directly describe the position and orientation of the image plane IP.

To determine the position an orientation of the image plane IP from the position and orientation of the sensor 120, sensor calibration data is used to transform the position and orientation of the sensor 120 to the position and orientation of the image plane IP. For simplicity, the term "position and orientation" is used to broadly refer to position and/or orientation. Accordingly, if the sensor 120 has the same orientation as the image plane IP, then the position and orientation calibration data may not contain any orientation calibration data. Similarly, as shown in FIG. 3, the sensor 120 may not have a positional offset with respect to one or more axes of the image plane IP.

There are a number of ways of defining the image plane/sensor offset. One method of calibrating at least some types of sensors use three orthogonal linear dimension offsets in X, Y, Z and three rotation angles about each of these axes. Other methods include using a position transformation matrix or quaternions, which are described in the user manual for the mini Bird™ and the Flock of Bird™ systems by Ascension Technology Corp.

As described above, the ultrasound probes with position and orientation sensors are typically used only with ultrasound systems that contain the calibration data for the probe/sensor pair. Conventionally, the probe/sensor pair is calibrated, and the calibration data is stored in the ultrasound system 100, which will be used in conjunction with the probe/sensor pair. If the probe/sensor pair is to be used with a different ultrasound system, then the probe/sensor pair typically needs to be re-calibrated on that different ultrasound system. Since sonographers are often unable or unwilling to perform probe/sensor pair calibration, probe/sensor pairs are often used only with the ultrasound system for which the probe/sensor pair was initially calibrated.

Referring back to FIG. 2, the beam former 113 may convert the electrical receive signals outputted from the ultrasound probe 112 into digital signals. The beam former 113 may further apply delays to the digital signals in consideration of the distances between the transducer elements and focal points to thereby output receive-focused signals.

The ultrasound data forming section 114 may form a plurality of ultrasound data by using the receive-focused signals. In one embodiment, the plurality of ultrasound data may be radio frequency (RF) data or IQ data. The image forming section 115 may form the three-dimensional ultrasound image of the target object based on the ultrasound data.

Referring back to FIG. 1, the sensor 120 may be mounted on one side of the ultrasound probe 112. In one embodiment, by way of non-limiting examples, the sensor 120 may be built in the ultrasound probe 112 to be away from the plurality of transducer elements (not shown) by a predetermined distance. Alternatively, the sensor 120 may be externally mounted on the ultrasound probe 112 to be away from the plurality of transducer elements. The sensor 120 may include three-dimensional sensor, which can detect a three-dimensional position and an angle of the ultrasound probe 112.

The memory 130 may store a three-dimensional CT image of the target object. In one embodiment, by way of non-limiting examples, the three-dimensional CT image may be a three-dimensional CT image of a liver in which a diaphragm and a blood vessel are extracted. The memory 130 may store information on a position between the three-dimensional ultrasound image and the sensor 120 (hereinafter, referred to as "position information"). The position information may include information on a distance between the transducer elements (not shown) and the sensor 120. In one embodiment, by way of non-limiting examples, the memory 120 may include at least one of a random access memory (RAM), a hard disk drive or the like.

The processor 140 may be configured to perform registration between the three-dimensional CT image and the three-dimensional ultrasound image, thereby forming a transformation function ($T_{probe}$) for representing the ultrasound probe 112 on the three-dimensional CT image. Furthermore, the processor 140 may perform calibration of the sensor 120 to match coordinates of the three-dimensional CT image (not shown) and coordinates of the sensor 120 based on the position information and the transformation function.

Figure 4:
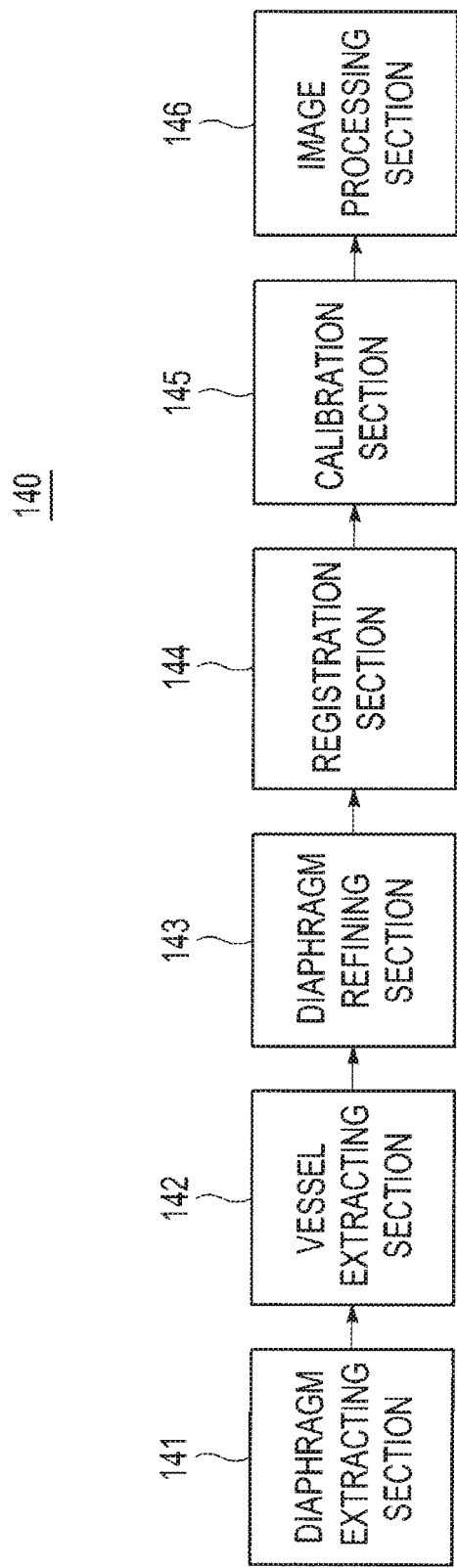
FIG. 4 is a block diagram showing an illustrative embodiment of a processor.

FIG. 4 is a block diagram showing an illustrative embodiment of the processor 140. The processor 140 may include a diaphragm extracting section 141, a vessel extracting section 142, a diaphragm refining section 143, a registration section 144, a calibration section 145 and an image processing section 146.

Figure 5:
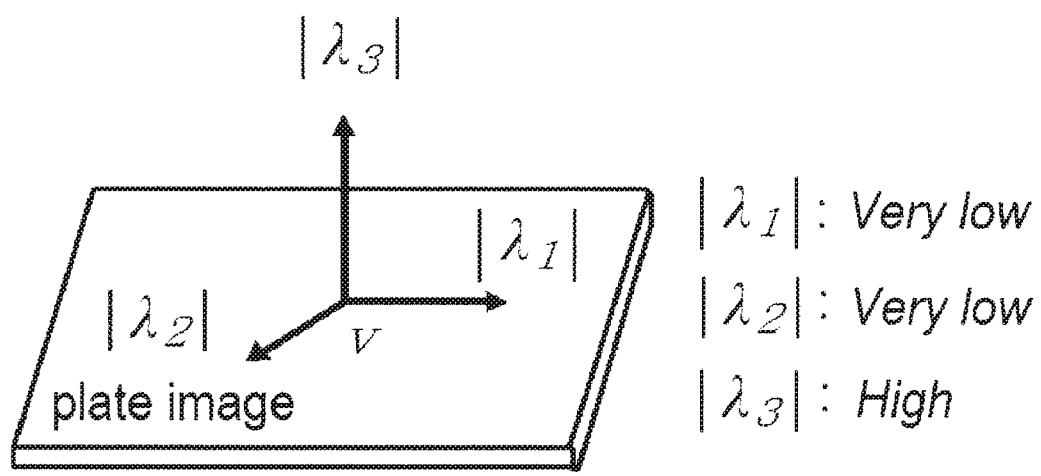
FIG. 5 is a schematic diagram showing an example of eigenvalues in the Hessian matrix.

The diaphragm extracting section 141 may be configured to extract a diaphragm from the three-dimensional ultrasound image formed in the ultrasound image forming unit 110. In one embodiment, the diaphragm extracting section 141 may perform a Hessian matrix based flatness test upon the three-dimensional ultrasound image to extract the diaphragm. The diaphragm may be considered as a curved surface in the three-dimensional ultrasound image. Thus, regions in which a voxel intensity change in a normal direction at a surface is greater than a voxel intensity change in a horizontal direction at the surface may be extracted as the diaphragm. FIG. 5 is a schematic diagram showing an example of eigenvalues $\lambda 1$, $\lambda 2$ and $\lambda 3$ in the Hessian matrix.

Hereinafter, an operation of the diaphragm extracting section 141 will be described in detail. The diaphragm extracting section 141 may be configured to select voxels having a relatively high flatness value. The flatness $\mu(v)$ may be defined as the following equation (1).

$$\mu(v) = \phi_1(v)\phi_2(v)\phi_3(v)/\phi_{3_{max}}(v) \quad (1)$$

wherein $\phi_1(v)$, $\phi_2(v)$ and $\phi_3(v)$ in the equation (1) may be represented as the following equation (2).

$$\phi_1(v) = \left(1 - \frac{\lambda_1(v)}{\lambda_3(v)}\right)^2, \phi_2(v) = \left(1 - \frac{\lambda_2(v)}{\lambda_3(v)}\right)^2, \phi_3(v) = \sum_i \lambda_i(v)^2 \quad (2)$$

wherein $\lambda_1$, $\lambda_2$ and $\lambda_3$ denote eigenvalues of the Hessian matrix at voxel v. The flatness $\mu(v)$ may be normalized to have values of ranging 0-1. A flatness map may be formed based on the flatness values obtained from all of the voxels according to the equations (1) and (2). Thereafter, the voxels having a relatively high flatness value are selected. In one embodiment, the voxels having the flatness over 0.1 may be selected.

The diaphragm extracting section 141 may be further configured to perform the morphological opening upon the selected voxels to remove small clutters therefrom. The morphological opening may be carried out by sequentially performing erosion and dilation. That is, a predetermined number of the voxels are removed in the edges of the area in which the voxels exist, and thus, the area becomes contracted (erosion). In this manner, it becomes possible to remove small clutters. Thereafter, the edges of the area are expanded by the predetermined number of the voxels (dilation). These erosion and dilation may be performed by one or more voxels.

The diaphragm is the largest surface in the three-dimensional ultrasound image. The largest surface may be selected among candidate surfaces obtained by the intensity-based connected component analysis (CCA) for the voxels and the selected surface may be regarded as the diaphragm in the three-dimensional ultrasound image. The voxel-based CCA is one of the methods of grouping regions in which voxel values exist. For example, the number of voxels connected to each of the voxels through a connectivity test by referring to values of voxels neighboring the corresponding voxel (e.g., 26 voxels) may be computed. The voxels, of which connected voxels are greater than the predetermined number, are selected as candidate groups. Since the diaphragm is the widest curved surface in the ROI, the candidate group having the most connected voxels may be selected as the diaphragm. The surface of the diaphragm may be smoothened.

The vessel extracting section 142 may be configured to perform vessel extraction upon the three-dimensional ultrasound image. The vessel extracting section 142 may be configured to perform the vessel extraction through ROI masking, vessel segmentation and classification.

To avoid mis-extraction of the vessels due to mirroring artifacts, the ROI masking may be applied to the three-dimensional ultrasound image by modeling the diaphragm as a polynomial curved surface. For example, the ROI masking may be used to model the diaphragm as the polynomial curved surface by using the least means square. However, if all of the lower portions of the modeled polynomial curved surface are eliminated, then meaningful vessel information may be lost at a portion of regions due to an error of the polynomial curved surface. To avoid losing the vessel information, the lower portion of the modeled polynomial curved surface may be eliminated with a marginal distance. For example, the marginal distance may be set to about 10 voxels at a lower portion of the ROI mask.

Subsequently, the vessel extracting section 142 may be further configured to segment a vessel region and a non-vessel region. To exclude non-vessel high intensity regions such as the diaphragm and vessel walls, a low intensity bound value having a less reference bound value in the ROI masked three-dimensional ultrasound image may be set as a reference bound value. Thereafter, voxels with a higher intensity value than the reference bound value may be removed. The remaining regions may be binarized by using an adaptive threshold value. Then, the binarized segments may be labeled as vessel candidates.

Next, the vessel extracting section 142 may be further configured to remove non-vessel-type clutters from the binarization image to form real vessel regions from the vessel candidates. In one embodiment, the vessel classification may include a size test, which evaluates the goodness of fit to a cylindrical tube, for filtering out tiny background clutters, a structure-based vessel test for removing non-vessel type clutters, i.e., an initial vessel test, a gradient magnitude analysis, and a final vessel test for precisely removing the clutters. Although some clutters are not removed through the structure-based vessel test, an initial threshold may be marginally set so that all vessels may be included. For example, a threshold value of the initial vessel test may be set to 0.6. At the final vessel test, clutters, which may be formed by small shading artifacts having low gradient magnitudes, may be precisely removed by considering variation of voxel values, i.e., gradient magnitudes, to thereby extract vessel data. In one embodiment, a threshold of the final vessel test may be set to 0.4.

The diaphragm refining section 143 may be configured to refine the diaphragm region by removing the clutters with the extracted vessel regions. The clutters are mainly placed near the vessel walls. Especially, the vessel walls of inferior vena cava (IVC) are more likely to be connected to the diaphragm and cause clutters. These clutters may degrade the accuracy of the feature based registration, and thus, it may be necessary to refine the diaphragm region. To refine the diaphragm, the vessel regions are extracted according to the vessel extraction mentioned above, the extracted vessel regions may be dilated, and then the dilated vessel regions may be subtracted from the initially extracted diaphragm region to estimate vessel walls. The estimated vessel walls may be removed from the diaphragm region. Finally, the diaphragm region may be extracted by applying CCA and the size test.

The registration section 144 may be configured to perform the image registration between the three-dimensional ultrasound and CT image. The registration section 144 may extract sample points from the vessel regions and the diaphragm region, respectively, among the features extracted from the three-dimensional ultrasound image. Also, after the vessel regions and the diaphragm region are extracted from the CT image, the registration section 144 may extract sample points from the vessel and the diaphragm region, respectively. The image registration between the three-dimensional ultrasound and CT image may be performed based on the extracted sample points to thereby form the transformation function ($T_{probe}$) between the three-dimensional CT image and the three-dimensional ultrasound image. The transformation function ($T_{probe}$) may be given by a matrix and used to transform a position of the ultrasound probe 112 to a corresponding position on the three-dimensional CT image.

The calibration section 145 may perform the calibration of the sensor 120 based on the transformation matrix ($T_{probe}$) from the registration section 144 and the position information stored in the memory 130. More particularly, the calibration section 145 may form a transformation matrix ($T_{sensor}$) between the sensor 120 and the three-dimensional ultrasound image, i.e., a transformation matrix representing a position of the sensor 120 with respect to the three-dimensional ultrasound image. The transformation matrix ($T_{sensor}$) may be given by a matrix. The transformation matrix ($T_{sensor}$) may be defined as the following equation (3).

$$T_{sensor} = \begin{vmatrix} r11 & r12 & r13 & x \\ r21 & r22 & r23 & y \\ r31 & r32 & r33 & z \\ 0 & 0 & 0 & 1 \end{vmatrix} \quad (3)$$

$r11 = \cos\theta y * \cos\theta z + \sin\theta x * \sin\theta y * \sin\theta z$ $r12 = \sin\theta z * \cos\theta y - \sin\theta x * \sin\theta y * \cos\theta z$ $r13 = \cos\theta x * \sin\theta y, r21 = \sin\theta z * \cos\theta x$ $r22 = \cos\theta z * \sin\theta x, r23 = \sin\theta x$ $r31 = \sin\theta z * \sin\theta x * \cos\theta y - \cos\theta z * \sin\theta y$ $r32 = -\cos\theta z * \sin\theta x * \cos\theta y - \sin\theta z * \sin\theta y$ $r33 = \cos\theta x * \cos\theta y$ wherein, x denotes coordinate of a lateral direction of the sensor 120, y denotes coordinate of an elevation direction of the sensor 120, z denotes an axial direction of the sensor 120, $\theta_x$ denotes an angle of the sensor 120 from the x-axis, $\theta_y$ denotes an angle of the sensor 120 from the y-axis, and $\theta_z$ denotes an angle of the sensor 120 from the z-axis. The elevation direction may be a swing direction of the transducer elements, the axial direction may be a scan line direction from the transducer elements and the lateral direction may be a longitudinal direction of the transducer elements.

The calibration section 145 may perform the calibration based on the transformation matrix ($T_{probe}$) and the transformation matrix ($T_{sensor}$). The calibration section 145 may form a transformation matrix (T) representing the position of the sensor 120 on the three-dimensional CT image. In one embodiment, the calibration section 145 may form the transformation matrix (T) through matrix multiplication of the transformation matrix ($T_{probe}$) and the transformation matrix ($T_{sensor}$).

The image processing section 146 may apply the transformation matrix (T) to the three-dimensional CT image to thereby form a two-dimensional CT image according to a two-dimensional ultrasound image.

Referring back to FIG. 1, the display unit 150 may display the two-dimensional CT image, which is provided from the processor 140. Furthermore, the display unit 150 may display the three-dimensional ultrasound image and the three-dimensional CT image.

Any reference in this specification to "one embodiment," "an embodiment," "example embodiment," "illustrative embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to affect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A medical imaging apparatus comprising:
a processor to generate an ultrasound image from a signal transmitted by an ultrasound probe, extract a certain anatomical feature from the ultrasound image and the certain anatomical feature from a medical image, perform a first registration between the medical image and the ultrasound image based on the certain anatomical feature, perform a second registration between a sensor coupled to the ultrasound probe and the medical image based on an ultrasound imaging position obtained by the sensor and the first registration, and control the display to display a portion of the ultrasound image corresponding to the ultrasound imaging position and a portion of the medical image corresponding to the ultrasound imaging position based on at least one of the first registration and the second registration, wherein the processor performs the first registration by matching the certain anatomical feature in the ultrasound image and the certain anatomical feature in the medical image.

2. The medical imaging apparatus of claim 1, wherein the processor is configured to obtain a first sample point of the certain anatomical feature extracted from the medical image of an object, obtain a second sample point of the certain anatomical feature extracted from the ultrasound image of the object, and perform the first registration between the medical image and the ultrasound image based on the first sample point and the second sample point.

3. The medical imaging apparatus of claim 1, wherein the ultrasound image is a three-dimensional (3D) ultrasound image,
the medical image is a volumetric medical image which includes two-dimensional (2D) medical images obtained over a region of an object,
the portion of the medical image includes one of the 2D medical images, and
the processor is further configured to control the display to display that one of the 2D medical images which corresponds to the ultrasound imaging position in the 3D ultrasound image, as indicated by the sensor.

4. The medical imaging apparatus of claim 1, wherein the processor is configured to obtain a first registration information which provides a relationship between a coordinate system of the medical image and a coordinate system of the ultrasound image based on the first registration, and calculate a first transform between the coordinate system of the medical image and the coordinate system of the ultrasound image, based on the first registration information, and
the first transform is applied to perform a conversion between the coordinate system of the medical image and the coordinate system of the ultrasound image.

5. The medical imaging apparatus of claim 4, wherein the processor is further configured to perform a third registration between the ultrasound image and the sensor, based on the ultrasound imaging position,
calculate a second transform which defines a relationship between a coordinate system of the sensor and the coordinate system of the ultrasound image, and
perform the second registration between the medical image and the sensor based on a combination function of the first transform and the second transform.

6. The medical imaging apparatus of claim 5, wherein the combination function is a product of the first transform and the second transform.

7. The medical imaging apparatus of claim 1, wherein the ultrasound probe comprises one of a three-dimensional ultrasound probe, a two-dimensional ultrasound probe, and a one-dimensional ultrasound probe.

8. The medical imaging apparatus of claim 1, wherein the sensor comprises a magnetic sensor to sense a position and an angle of a transducer mounted to the ultrasound probe.

9. The medical imaging apparatus of claim 1, wherein the processor is configured to generate the ultrasound image of an object including a liver.

10. The medical imaging apparatus of claim 1, wherein the ultrasound image and the medical image are three-dimensional images.

11. The medical imaging apparatus of claim 10, wherein the certain anatomical feature is included in a surface area imaged inside an object, and
the processor is configured to extract the surface area from the medical image of the object, extract a portion of a corresponding surface area from the ultrasound image of the object, and perform the first registration between the medical image and the ultrasound image by matching one or more points of the surface area extracted from the medical image with one or more points of the portion of the corresponding surface area extracted from the ultrasound image.

12. The medical imaging apparatus of claim 10, wherein the certain anatomical feature is included in a vessel, and
the processor is further configured to extract the vessel from the medical image of an object, extract a portion of a corresponding vessel from the ultrasound image of the object, and perform the first registration between the medical image and the ultrasound image by matching one or more points of the vessel extracted from the medical image with one or more points of the portion of the corresponding vessel extracted from the ultrasound image.

13. The medical imaging apparatus of claim 12, wherein the processor is further configured to extract the vessel from the medical image of the object by segmenting the vessel from a region of the object containing a vessel portion and a non-vessel portion in the medical image, and extract the portion of the corresponding vessel from the ultrasound image of the object by segmenting the portion of the corresponding vessel from the region of the object containing the vessel portion and the non-vessel portion in the ultrasound image.

14. The medical imaging apparatus of claim 1, wherein the processor is configured to extract the certain anatomical feature from the medical image which has been acquired by a medical imaging modality which captures imaging data via an imaging technique different from that of an ultrasound apparatus.

15. A medical imaging method comprising:
generating an ultrasound image from a signal transmitted by an ultrasound probe;
extracting a certain anatomical feature from the ultrasound image and the certain anatomical feature from a medical image;
performing a first registration between the medical image and the ultrasound image, based on the certain anatomical feature;
performing a second registration between a sensor coupled to the ultrasound probe and the medical image, based on an ultrasound imaging position obtained by the sensor and the first registration; and
controlling a display to display a portion of the ultrasound image corresponding to the ultrasound imaging position and a portion of the medical image corresponding to the ultrasound imaging position, based on at least one of the first registration and the second registration,
wherein the performing of the first registration comprises matching the certain anatomical feature in the ultrasound image and the certain anatomical feature in the medical image.

16. The medical imaging method of claim 15, wherein the performing the first registration comprises:
obtaining a first sample point of the certain anatomical feature extracted from the medical image of an object;
obtaining a second sample point of the certain anatomical feature extracted from the ultrasound image of the object; and
performing the first registration between the medical image and the ultrasound image based on the first sample point and the second sample point.

17. The medical imaging method of claim 15, wherein the ultrasound image is a three-dimensional (3D) ultrasound image, the medical image is a volumetric medical image which includes two-dimensional (2D) medical images obtained over a region of an object, the portion of the medical image includes one of the 2D medical images, and the display is controlled to display that one of the 2D medical images which corresponds to the ultrasound imaging position in the 3D ultrasound image, as indicated by the sensor.

18. The medical imaging method of claim 15, further comprising:

obtaining a first registration information which provides a relationship between a coordinate system of the medical image and a coordinate system of the ultrasound image based on the first registration; and calculating a first transform between the coordinate system of the medical image and the coordinate system of the ultrasound image, based on the first registration information, wherein the first transform is applied to perform a conversion between the coordinate system of the medical image and the coordinate system of the ultrasound image.

19. The medical imaging method of claim 18, further comprising:

performing a third registration between the ultrasound image and the sensor, based on the ultrasound imaging position; and calculating a second transform which defines a relationship between a coordinate system of the sensor and the coordinate system of the ultrasound image, wherein the performing the second registration comprises performing the second registration between the medical image and the sensor based on a combination function of the first transform and the second transform.

20. The medical imaging method of claim 19, wherein the combination function is a product of the first transform and the second transform.

* * * * *